United States Patent [19]

Steffen et al.

[11] Patent Number: 4,673,751

[45] Date of Patent: Jun. 16, 1987

[54] METHOD OF PREPARING 3,4-DIHYDRO-ALPHA-PYRONES

[75] Inventors: Klaus-Dieter Steffen, Hennef; Günther Meyer, Troisdorf, both of Fed. Rep. of Germany

[73] Assignee: Dynamit Nobel AG, Troisdorf, Fed. Rep. of Germany

[21] Appl. No.: 673,921

[22] Filed: Nov. 21, 1984

[30] Foreign Application Priority Data

Nov. 25, 1983 [DE] Fed. Rep. of Germany ....... 3342598

[51] Int. Cl.[4] ............................................ C07D 309/32
[52] U.S. Cl. .................................................... 549/294
[58] Field of Search ......................................... 549/294

[56] References Cited

U.S. PATENT DOCUMENTS 4,562,270 12/1985 Schmidt .............................. 549/294

FOREIGN PATENT DOCUMENTS 2952068 7/1981 Fed. Rep. of Germany .
3138843 4/1983 Fed. Rep. of Germany .

OTHER PUBLICATIONS

Hackh's Chemical Dictionary, 4th Edition, p. 734.

Primary Examiner—Norma S. Milestone
Attorney, Agent, or Firm—Felfe & Lynch

[57] ABSTRACT

A method for the preparation of 3,4-dihydro-alpha-pyrones by the thermolysis of 5-hydroxymethyl-gamma-butyrolactone in a liquid medium at temperatures between 300° and 400° C. and in the presence of aluminosilicates as catalysts is disclosed. The dihydropyrone that forms is distilled out of the reaction medium together with the reaction water immediately after its formation. Heat transfer oils, including, for example, polynuclear aromatic compounds joined together by methylene bridges or other bridge groupings, are especially suitable as heat transfer oils. The method has the advantage of permitting the temperature to be regulated within a definable range so that secondary reactions due to local overheating or imprecise temperature control occur to only a limited degree if at all.

4 Claims, No Drawings

METHOD OF PREPARING 3,4-DIHYDRO-ALPHA-PYRONES

The subject matter of the present invention is a method of preparing 3,4-dihydro-alpha-pyrones of the general formula

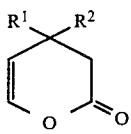

(1)

wherein the moieties $R^1$ and $R^2$ represent low alkyl moieties and/or hydrogen atoms, by heating 5-hydroxymethyl-gamma-butyrolactones of the general formula

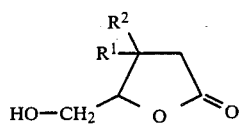

(2)

at temperatures up to 600° C. in the presence of aluminosilicates.

The preparation of 3,4-dihydro-alpha-pyrones of Formula I by the thermolysis of 5-hydroxymethyl-gamma-butyrolactones of Formula II is described, for example, in German Offenlegungsschriften Nos. 29 52 068 and 31 38 843. In the method described in these patents, the use of solvents is mentioned; but the solvents named therein all boil below 200° C. and serve only for dissolving the starting compound (II) or as a gaseous withdrawing agent. The preparation is described thus: the starting compound is put through a heated tube that is filled with silicatic materials. It is known, however, that an accurate temperature control that is constant and uniform longitudinally and transversely in such reactors, in which heat tones—of an endothermic or exothermic nature—also occur, is extremely difficult on account of poor thermal gradients, at least in the larger tube diameters.

It is furthermore known that temperature differences of approximately 10° entail a halving or doubling of the reaction rate (van't Hoff), so that in the procedures described in the above disclosures, due to the necessarily occurring temperature gradients within the tube, greatly differing reaction rates occur: undesirable secondary reactions are therefore inevitable.

It is also a disadvantage of this method that the finished product, which is formed at the beginning of the reaction tube, has to be carried through the entire tube length and catalyst packing, and at the same time is exposed to the high reaction temperatures with their possible negative effects.

The problem therefore existed, in the production of 3,4-dihydro-alpha-pyrones by the thermolysis of 5-hydroxymethyl-gamma-butyrolactones, to conduct the reaction such that the reaction components will be reacted within a precise temperature range that is as uniform as possible, during a variable time of stay in the reactor, and such that the desired end product will be exposed for the shortest possible time to the elevated temperatures.

THE INVENTION

As a solution to this problem, a method has now been found for the preparation of 3,4-dihydro-alpha-pyrones by heating 5-hydroxymethyl-gamma-butyrolactones at temperatures up to 600° C. in the presence of catalysts, which is characterized by heating the 5-hydroxymethyl-gamma-butyrolactones in a liquid medium at temperatures between 300° and 400° C. in the presence of aluminosilicates.

Solvents are used as the liquid reaction medium which have boiling points above 200° C. In the case of solvents which boil below the reaction temperature, the process can be performed under pressure, and the target product (I) as well as the water that is formed in the thermolysis can be distilled out through a pressure-maintaining valve.

The solvents which can be used in accordance with the invention are to be associated generally with the heat transfer oils. These can be of either natural or synthetic origin. Examples are: mineral oil raffinates, paraffins, polycyclic hydrocarbons or polynuclear aromatics. The polynuclear aromatics can be bonded to one another either directly or through groupings from the group: —$CH_2$—, —O —, —$SO_2$—, —$OSiR_2O$— (R =alkylene). Corresponding, partially hydrogenated or chlorine-substituted polynuclear aromatics can also be used. As a rule, isomer mixtures or mixtures of different chemical structure are used for the purpose of reducing the melting range.

The catalyst is suspended by stirring it in these solvents. The catalyst is an aluminosilicate with any desired geometrical form, e.g , in the form gf spheres, rodlets or even in powder form. Aluminosilicates are those silicates in which the silicon atoms are replaced partially by aluminum atoms in the lattice structure, and the residual charges are equalized by potassium, sodium or calcium ions. They have pore sizes from 2 to 20 Angstroms and can be of natural or synthetic origin.

The catalyst must furthermore be selected so that it does not decompose the high-boiling solvent. For example, when polynuclear aromatics bound together by —$CH_2$— bridges are used, zeolites are particularly well suited as catalysts, while montmorillonites in this case have a degrading action. In other words, it must always be determined by preliminary experiment whether the aluminosilicate to be used in each case is compatible with the solvent at the claimed temperatures.

The desired high yields of the end product are obtained only in the temperature range of 300 ° to 400° C. At lower temperatures the yields are considerably lower, while operating at higher temperatures leads to more degradation products.

The weight ratio of solvent to aluminosilicate can be selected within the limits of 2:(0.2 to 2.0), but preferably of 2:(0.8 to 1.0).

In the actual practice of the present method, the starting product (II) is fed in melted form, in portions or continuously, to the mixture of solvent and catalyst, heated to the desired reaction temperature, and the target product (I) is distilled out with the water as quickly as possible after its formation. When distilling the target product together with the water out of the reaction medium, it is desirable—in order to avoid taking starting product and solvent out along with it—to insert a dephlegmator in a known manner, keeping it at the boiling temperature of the end product (I).

During the reaction adequate stirring is maintained to assure good thermal gradients and good substance exchange. Inertiation can be performed with a small current of nitrogen.

After the end product has been distilled out of the reaction medium along with the water formed in the reaction, it is separated from the water by distillation in a manner known in itself. In general, on account of the insolubility of the pyrones in the water, a mechanical separation of the two components can be performed. Then the 3,4-dihydro-alphapyrone is fractionally distilled. Yields around 70% of the theory, with respect to the input 5-hydroxymethyl-gammabutyrolactone, are achieved.

Many times the amount of the lactone (II) can be used per unit amount of catalyst. Even if the catalyst mixture turns black, the mixture is still fully reactive, and its usefulness is limited only by a gradual increase in viscosity to the point where it cannot be stirred.

After the reaction has ended, the catalyst can be regenerated. This is accomplished by filtering it out, washing it with simple solvents (e.g., acetone) and then heating to incandescence; thereafter the catalyst is again completely usable. For reasons of cost, however, the simple dumping or destruction of the final bottoms of catalyst and solvent is advisable.

The substituted 3,4-dihydro-alpha-pyrones are important intermediates for the synthesis of highly effective insecticides.

EXAMPLES

EXAMPLE 1

In a one-liter four-necked flask provided with stirrer, thermometer, heatable dropping funnel and fractionating column, 200 grams of an isomer mixture of polynuclear aromatics linked together by —$CH_2$— bridges (commercially obtainable under the name "Marlotherm S") and 90 g of zeolite in ball form with a 5-angstrom pore size are placed, and heated at 350° C. The lower part of the fractionating column consisted of a Vigreux column heated at about 220° C. Over a period of 30 minutes, 60 g of 4,4-dimethyl-5-hydroxymethyl-gamma-butyrolactone (OH-V) was added drop by drop and allowed to react for another 30 minutes, while the 3,3-dihydro-4,4-dimethyl-alpha-pyrone (DDP) and the water of condensation distilled out through the fractionating column. This proportioning of the OH-V was repeated 30 times, so that a total of 1.8 kg of the starting substance was put through.

The DDP that distilled out was condensed together with the water that distilled out, the water phase was separated, and the organic phase was distilled through a column (B.P. 69° C./14 Torr). 1150 g of 3,4-dihydro-4,4-dimethyl-alphapyrone (DDP) with a purity of 97% was obtained, which corresponds to a yield of 70.8% of the theory with respect to the input OH-V. If allowance is made for the unreacted and recovered amount of the OH-V, the yield is 73.1% of the theory.

EXAMPLE 2

The catalyst used in Example 1 was filtered out on a coarse frit filter, washed well with acetone, and heated to incandescence overnight at 500° C. Example 1 was then repeated under the same conditions, with the catalyst regenerated in this manner. of 4,4

However, only 1.2 kg dimethyl-5-hydroxymethyl-gamma-butyrolactone was put through.

807 g of 3,4-dihydro-4,4-dimethyl-alpha-pyrone with a purity of 98% was obtained. Yield: 75.3% of the theory with respect to input OH-V; after withdrawal of the recovered starting product the yield is 78.2% of the theory.

EXAMPLE 3

In the apparatus of Example 1, 200 g of the isomer mixture named in Example 1 and 90 g of a zeolite having a pore size of 9 angstroms were heated at 350° C. and a total of 1.8 kg of 4,4-dimethyl-hydroxy-gamma-valerolactone was put through in portions of 60 g each. After separation of the reaction water the organic phase was fractionated. 1091 g of DDP was obtained, with a purity of 97%. Yield: 67.2% of the theory; after deduction of recovered OH-V: 70.0% of the theory.

EXAMPLE 4

An apparatus was constructed which consisted of a 6liter multi-necked flask with stirrer, thermometer, a dephlegmator maintained at about 220° C., and a fractional distillation column as well as an immersion tube, and which could be supplied continuously with product from a heated tank. The apparatus was inertiated with a slow flow of nitrogen. 1.2 kg of the isomer mixture specified in Example 1, and 540 g of a zeolite with a pore size of 5 angstroms were placed and heated at 350° C. Then, at a rate of about 350 g/h, a total of 23.2 kg of 4,4-dimethyl-5-hydroxymethyl-gamma-butyrolactone was fed into it continuously from the heated supply tank, and DDP was distilled out accordingly with the reaction water. Then the reaction water was separated and the organic phase distilled for purification. Yield: 13.3 kg of DDP with a purity of 97%, corresponding to 63.6% of the theory.

EXAMPLE 5

In the laboratory apparatus of Example 1, 200 g of the isomer mixture specified in that example, and 90 g of a zeolite in the form of pellets of 1 mm diameter and a pore size of 5 angstroms were placed and heated at 350° C. At intervals of one hour, 6.0 kg of 4,4-dimethyl-5-hydroxymethyl-gamma-butyrolactone was fed in in 60-gram portions. The product was worked up as in Example 1 and the DDP was isolated. Yield: 3742.5 g of DDP with a purity of 97.5%, corresponding to 69.5% of the theory.

EXAMPLE 6

This experiment was performed as in Example 5, except that the reaction was performed at 370° C. and stopped after 1.2 kg of OH-V had been added. Yield: 718 g of DDP, purity 98%, corresponding to 67.0% of the theory.

EXAMPLE 7

In a 120-liter high-grade steel stirring vessel (immersion tube, dephlegmator, condenser with receivers), 35 kg of the solvent described in Example 1 and 15 kg of a calcium-sodium-aluminum silicate were placed and heated at 340° to 350° C. A total of 205.5 kg of 4,4-dimethylhydroxy-gamma-valerolactone was added continuously through the immersion tube from a heated supply tank by means of a proportioning pump at a rate of 5 kg/h at first and 8 kg/h afterwards. As the proportioning progressed, the reaction water and 3,4-dihydro-4,4-dimethyl-alpha-pyrone distilled out. The water was separated and the organic phase was purified by distillation in a larger laboratory column. Yield: 130.6 kg with a purity of 95%, corresponding to 69.2% of the theory with respect to valerolactone input. A total of about 2 kg of valerolactone was recovered, which was used in the next batch.

It will be understood that the specification and examples are illustrative but not limitative of the present invention and that other embodiments within the spirit and scope of the invention will suggest themselves to those skilled in the art.

We claim:

1. A method of preparing 3,4-dihydro-alpha-pyrones of the general formula

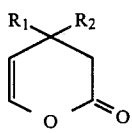

in which $R^1$ and $R^2$ represent low alkyl moieties of 1 to 4, or hydrogen, by heating 5-hydroxymethyl-gamma-butyrolactones of formula II

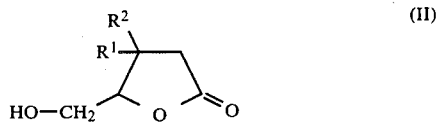

in which $R^1$ and $R^2$ have the meaning given above, comprising heating the 5-hydroxymethyl-gamma-butyrolactones in a liquid heat transfer oil at temperatures between 300° and 400° C. in the presence of a zeolite catalyst, said liquid heat transfer oil being a polynuclear aromatic compound wherein the aromatic groups are linked to one another directly or through a grouping selected from the group consisting of —$CH_2$—, —O—, —$SO_2$—, or $OSiR_2O$, R being alkylene, said liquid heat transfer oil having a boiling point above 200° C. and remaining liquid during the heating; distilling the 3,4-dihydro-alpha-pyrone out of the reaction medium immediately upon its formation; and feeding the butyrolactone (II) into the liquid heat transfer oil in the measure in which the pyrone (I) is distilled out.

2. The method of claim 1, wherein the ratio of liquid heat transfer oil to zeolite catalyst is 2:(0.2 to 2.0).

3. The method of claim 2 wherein the ratio of liquid heat transfer oil to zeolite catalyst is 2:(0.8 to 1.0).

4. The method of claim 1, wherein $R^1$ and $R^2$ are low alkyl moieties of 1 or 2 carbon atoms.

* * * * *